(12) United States Patent
Antrim et al.

(10) Patent No.: US 6,670,155 B2
(45) Date of Patent: Dec. 30, 2003

(54) PROCESS FOR PREPARING DEXTRINS

(75) Inventors: Richard L. Antrim, Solon, IA (US); Clark P Lee, Blue Grass, IA (US)

(73) Assignee: Grain Processing Corporation, Muscatine, IA (US)

( * ) Notice: Subject to any disclaimer, the term of this patent is extended or adjusted under 35 U.S.C. 154(b) by 0 days.

(21) Appl. No.: 09/795,996

(22) Filed: Feb. 28, 2001

(65) Prior Publication Data

US 2001/0046690 A1 Nov. 29, 2001

Related U.S. Application Data

(60) Provisional application No. 60/185,474, filed on Feb. 28, 2000.

(51) Int. Cl.$^7$ .................................................. C12P 19/22
(52) U.S. Cl. ............................ 435/95; 435/72; 435/99; 435/101; 536/103
(58) Field of Search ............................... 435/72, 95, 99, 435/101; 536/103

(56) References Cited

U.S. PATENT DOCUMENTS

| | | |
|---|---|---|
| 3,705,039 A | 12/1972 | Mitsuhashi et al. |
| 3,795,584 A | 3/1974 | Mitsuhashi et al. |
| 3,804,715 A | 4/1974 | Sugimoto et al. |
| 3,832,285 A | 8/1974 | Kurimoto |
| 4,001,435 A | 1/1977 | Hirao et al. |
| 4,028,186 A | 6/1977 | Sakai |
| 4,032,403 A | 6/1977 | Sakai et al. |
| 4,487,198 A | 12/1984 | Miyake et al. |
| 4,511,654 A | 4/1985 | Rohrbach et al. |
| 4,780,149 A | 10/1988 | Kaper et al. |
| 4,816,445 A | 3/1989 | Mitsuhashi et al. |
| RE33,047 E | 9/1989 | Miyake et al. |
| 4,977,252 A | 12/1990 | Chiu |
| 5,112,407 A | 5/1992 | Sakai et al. |
| 5,185,176 A | 2/1993 | Chiu |
| 5,482,560 A | 1/1996 | Ammeraal et al. |
| 5,562,937 A | 10/1996 | Senkeleski et al. |

FOREIGN PATENT DOCUMENTS

| | | |
|---|---|---|
| EP | 0 242 913 A3 | 10/1987 |
| EP | 0 332 027 A1 | 9/1989 |
| EP | 1 016 728 A2 | 7/2000 |
| WO | WO 95/10627 | 4/1995 |
| WO | WO 01/16348 A1 | 3/2001 |
| WO | WO 01/16349 A1 | 3/2001 |

OTHER PUBLICATIONS

Sugimoto et al., "Manufacture of Maltose with Yeasts," *Patent Abstract* (JP 05219977) (1993).
Takahashi et al., "Manufacture of High Purity maltose Aqueous Solutions," *Patent Abstract* (JP 04271793) (1992).
Maruo et al., "A Novel and Efficient Method for Enzymic Synthesis of High Purity Maltose Using Moranoline (1–Deoxynojirimycin)," *Chem. Lab.*, 56(9), 1406–1409 (1992).
Nehete et al., "An Optimized Protocol for the Production of High Purity Maltose,"*Worl J. Microbol, Biotechnol*, 8(4), 446–450 (1992).
Niimi et al., "Enzymic Manufacture of High–Purity Maltose from Starch," *Patent Abstract* (JP 4158795) (1992).
Niimi et al., "Preparation of High–Purity Maltose by Crystallization," *Patent Abstract* (JP 03228688) (1991).
Niimi et al., "Enzymatic Manufacture of Highly Pure Maltose and its Hydrolyzate," *Patent Abstract* (JP 02119789) (1990).
Sakai et al., "Process for Preparing Maltose Powder," *Patent Abstract* (EP 88–304743) (1988).
Goodman, "Process for Separating Maltose from Mixtures of Maltose, Glucose and Other Saccharides," *Patent Abstract* (U.S. 4,707,190) (1987).
Takasaki, "High Maltose Preparation," *Patent Abstract* (JP 60186296) (1985).
Miyake et al., "High Purity Maltose," *Patent Abstract* (FR 2510581) (1983).
Walon, "Maltose–Containing Starch Hydrolyzate and Crystallization of Maltose Therefrom," *Patent Abstract* (U.S. 4,199,372) (1980).
Konishi et al., "Maltase Having High Purity," *Patent Abstract* (JP 53118532) (1978).
Okada et al., "Maltose of High Purity," *Patent Abstract* (JP 7757344) (1977).
Takasaki, "High Purity Maltose," *Patent Abstract* (JP 7707487) (1977).
Takasaki, "High Purity Maltose," *Patent Abstract* (JP 7707486) (1977).
Yabuki et al., "Preparing Maltose," *Patent Abstract* (JP 76101141) (1976).
Murayama et al., "Maltose," *Patent Abstract* (JP 7698346) (1976).
Sakai, "Starch–Saccharified Product Having High Maltose–Purity," *Patent Abstract* (JP 51070833) (1976).
Mitsuhashi, "Production of Very Pure Maltose from Starch," *Patent Abstract* (FR 2012831) (1970).
Mitsuhashi, "High–Purity Maltose from Starch," *Patent Abstract* (ZA 6904923) (1970).
Kurimoto et al., "Highly Pure Crystalline Maltose from Starch," *Patent Abstract* (DE 1958014) (1970).

(List continued on next page.)

*Primary Examiner*—Francisco Prats
(74) *Attorney, Agent, or Firm*—Scott A. Burow; Banner & Witcoff, Ltd.

(57) ABSTRACT

Dextrins are prepared by hydrolyzing starch with an enzyme that consists essentially of a beta-amylase enzyme. The product prepared thereby will include a dextrin, such as beta-limit dextrin. Upon ultrafiltration of this product, a dextrin-rich fraction may be recovered. If desired, the dextrin-rich fraction may be further purified via diafiltration. Retrograded amylose may be separated from the product of enzymatic hydrolysis.

3 Claims, No Drawings

OTHER PUBLICATIONS

Hayashibara Co., Ltd., "High–Purity Maltose," *Patent Abstract* (JP 19670630) (1969).

Sugimoto et al., "High–Purity Maltose by Removing Contaminating Glucose with Yeast," *Patent Abstract* (JP 61104794) (1986).

Akio et al., "Studies on Production of Maltose by Membrane Separation Technique," *Chemical Abstracts Service*, DN 93:148430 (XP–002177602) (1979).

Ghiasi et al., "Note on the Hydrolysis of Amylose by Beta–Amylase," *Starch/Stärke, Dep. of Grain Sci. & Ind.*, Kansas State Univ., 33 (12), pp. 428–430 (XP–002177601) (1981).

Peat et al., Enzymatic Synthesis and Degradation of Starch. β–Amylase and the Constitution of Amylose. Part XV. J. Chem. Soc. 1952, 705–713.

PROCESS FOR PREPARING DEXTRINS

RELATED APPLICATION

This application claims priority to prior provisional application Ser. No. 60/185,474, filed of Feb 28, 2000, the entire contents of which are hereby incorporated by reference.

TECHNICAL FIELD OF THE INVENTION

This invention is in the field of oligosaccharides, and in particular, the invention pertains to the preparation of a high molecular weight dextrin product.

BACKGROUND OF THE INVENTION

Certain enzymes, known as beta-amylase enzymes, are known to act on starch to produce low molecular weight species, typically maltose, and high molecular weight species, known as dextrins. With the exception of so-called waxy (corn) or glutinous (rice) starches, most starches found in nature are composed of a mixture of amylopectin and amylose. Amylose is a linear molecule which is substantially completely hydrolyzed by beta-amylase enzymes into maltose and glucose. Amylopectin, a branched molecule, is hydrolyzed into maltose and higher molecular weight dextrins, because the beta-amylase enzyme is unable to hydrolyze past the alpha 1-6 branch point in the amylodextrin molecule. If the enzymatic hydrolysis is allowed to proceed to its fullest extent, the remainder of the amylopectin molecule will exist as what is known as beta-limit dextrin.

Despite the potentially numerous commercial uses for such high molecular weight dextrins, it is believed that no such dextrins are sold commercially in bulk quantities. Present enzymatic processes yield a mixture of products from which it is difficult to resolve such dextrins. The present invention seeks to provide a process for preparing dextrins, such as beta-limit dextrin, in which this difficulty is overcome.

THE INVENTION

It has now been found that the treatment of starch with an enzyme that consists essentially of a beta-amylase enzyme, and which is to the substantial exclusion or complete exclusion of alpha-amylase enzymes and de-branching enzymes, will yield a product mixture that includes a dextrin and one or more low molecular weight sugars. The low molecular weight sugar or sugars may be readily separated from the product mixture thus formed via ultrafiltration to yield a dextrin in the retentate. If desired, diafiltration may be used to separate substantially all of the low molecular weight sugars from the dextrin in the retentate.

Retrograded amylose may be removed from the product mixture prior to ultrafiltration. In accordance with another embodiment, the invention provides a method for preparing retrograded amylose. It is contemplated that this material is useful as "resistant" starch, which is not as digestible as other starches and which therefore may be used as a low- or non-caloric bulking agent.

The dextrins thus prepared will have a number of desirable properties, including a high solubility and a high molecular weight, with low hazing in solution. Additionally, the dextrins have a very low dextrose equivalent value (DE), and thus are expected to be substantially more stable than carbohydrates of lower molecular weight. As such, it is contemplated that such dextrins may be used in applications such as viscosifiers or as spray drying aids for other carbohydrates (such as maltose). In accordance with another embodiment of the invention, the dextrin is added to maltose in an amount sufficient to assist in spray drying.

DESCRIPTION OF THE PREFERRED EMBODIMENTS

The invention contemplates the production of dextrins, such as beta-limit dextrin, from starch. Any suitable starch may be employed in connection with the invention, and thus, for instance, starches such as corn, rice, wheat, tapioca, maize, potato, barley, oat, and, more generally, any starch suitable for enzymatic hydrolysis may be used in connection with the invention. It is not necessary to use a so-called waxy or glutinous starch in connection with the invention, but to the contrary the starch can have any suitable amylose content, such as an amylose content of 10%, 15%, 20%, 25%, or a greater amylose content. It is contemplated that the starch may be a partially derivatized or otherwise modified starch, or may be a starch that has been thinned or enzymatically treated. For instance, a starch that has been lightly oxidized may be employed.

The starch should be liquefied via heat, enzymatic, or acid treatment prior to treatment with the beta-amylase enzyme. Preferably, the starch is liquefied via acid treatment, although low amylose starches may require liquefaction only with heat and may be suitably liquefied at the operating temperature of the enzymatic hydrolysis. As disclosed in more detail in copending application Ser. No. 09/796,027, filed Feb. 28, 2001 by Richard L. Antrim and Clark P. Lee and hereby incorporated by reference, it is desirable to recover maltose from the beta-amylase hydrolysis product. Thus, in general, the starch should be liquefied to an extent such that it would remain liquid at the operating temperature of the beta-amylase hydrolysis, but not liquefied to an extent such that the starch is converted to saccharides having so low a degree of polymerization that it is difficult to separate such saccharides from maltose via ultrafiltration. In other words, the degree of liquefaction should be such that, upon enzymatic hydrolysis with the beta-amylase enzyme, the combined content of glucose and oligosaccharides in the DP 3–10 range does not (exceed about 10%, and preferably does not exceed about 5%. It has been found acceptable to liquefy the starch to a dextrose equivalent (DE) value of about 2, as measured via conventional techniques. Generally, the DE of the starch should be kept below about 1, and thus the DE should range between 0 and about 1, although it may be difficult to measure the DE with precision in this range. For corn starch, it is preferable that the starch is liquefied in an aqueous solution at a liquefaction temperature ranging from about 220° F. to about 320° F., and for a time ranging from about 5 minutes to about 30 minutes.

The starch solids level preferably ranges initially from about 5% to about 30%, more preferably, from about 15% to about 30%. While it is not intended to limit the invention to a particular theory of operation, it is believed that a lower solids content requires a lesser degree of liquefaction to attain the desired viscosity range. In the case of dent corn starch, it has been found that a viscosity window of between 25 and 45 centipoise (Norcross Shell Cup) is optimal. In the case of waxy starches, viscosities outside this range may be acceptable. The pH of the starch slurry should be adjusted to a level sufficient to provide controlled acid hydrolysis of the starch in the presence or absence of catalyzing alpha amylase enzymes; most preferably, under a given set of conditions, the variability of the slurry pH should be no more than +/−0.1 pH, with the precise pH value depending upon the starch source, the slurry solids, and the operational conditions of the liquefaction equipment employed. As a practical matter, the pH can vary more widely while still resulting in a satisfactory product. Preferably, the starch liquefaction is monitored via viscosity and adjusted accordingly.

In accordance with one embodiment of the invention, the starch is liquefied with an alpha-amylase enzyme to reduce the molecular weight of the starch, thereby reducing the viscosity of the starch and thereby permitting processing at a higher solids level. Suitable commercial liquefying enzymes may be obtained from Genencor International, Inc. or from Novozymes A/S. The dosing level of the alpha-amylase enzyme depends upon the desired solids level and, when maltose is recovered as a co-product, on the desired maltose purity. Desirably, the dosing level ranges from about 0.005% to about 0.02% of a commercial strength enzyme by dry solids basis starch. In this embodiment, the alpha-amylase enzyme preferably is quenched prior to saccharification via any suitable quenching procedure. For instance, when the starch is liquefied at a temperature less then 250° F. and 5 minutes residence, the alpha-amylase enzyme is quenched by reducing the liqefact pH to less than 4.0 and holding at a temperature of from 180 to 190° F. for at least about 15 minutes.

Upon liquefaction, the liquefact is immediately cooled and the pH is adjusted to the optimum conditions for beta-amylase activity. The starch then is treated with the enzyme under any conditions suitable to result in the hydrolysis of this liquefied starch to form dextrin, and preferably, to form beta-limit dextrin. A preferred enzyme is OPTIMALT BBA, available from Genencor International, Inc. The enzyme may be added in any amount sufficient to achieve this result, but generally, the dosing of the enzyme should be in excess of the minimum viscosity limited conversion of approximately two Genencor OPTIMALT BBA Diastatic Power units per kilogram of starch, tile Diastatic Power units being defined as being the amount of enzyme contained in 0.1 ml of a 5% solution of the sample enzyme preparation that will provide sufficient reducing power to reduce 5 ml of Fehling's solution when the sample is incubated with 100 ml of substrate for one hour at 20° C.

The enzymes should be allowed to act on the starch for any amount of time suitable to form the desired dextrin. Under the preferred reaction conditions discussed hereinabove, the enzymatic action generally is 90% complete within 4 hours. The optimum temperature and pH of the starch hydrolysis will vary depending on the particular beta-amylase enzyme employed, but typically the temperature will range from about 55° C. to about 65° C. and the pH will range from about 5.0 to about 6.0. Optionally, but preferably, the product mixture thus formed is clarified and decolored by any suitable procedure, such as carbon treatment, filtration, centrifugation, and or precipitation, before it is further processed. If the enzyme is allowed to act under optimum conditions for an optimum reaction time, the dextrin content may be greater than about 20%, most of which will comprise beta-limit dextrin. The combined content of glucose and of oligosaccharides in the DP 3–10 range is below about 10%, and preferably is below 5%.

Retrograded amylose may be found as a by-product of the enzymatic hydrolysis. In accordance with one embodiment of the invention, at least some of the retrograded amylose is separated from the product mixture. For instance, the saccharified solution may be maintained at a temperature below about 140° F. to allow at least a portion of the retrograded amylose to crystallize. The crystallized amylose then may be separated from the saccharified starch mixture by any suitable technique, such as via microfiltration, by which is contemplated separation at a resolution sufficient to separate the retrograded amylose but not sufficient to separate dextrins from low molecular weight sugars in the product mixture. Alternatively, the retrograded amylose may be separated via centrifugation, using any technique known in the art or otherwise found to be suitable. Preferably, the solution prepared upon enzymatic hydrolysis is centrifugated for at least 15 minutes at a relative g force of 3000. The amylose crystals will form a pellet, and the low molecular weight sugars and limit dextrin will remain in the clarified supernate.

In accordance with one embodiment of the invention, a dextrin is separated from the product mixture. Most preferably, a dextrin product is separated from the product mixture via ultrafiltration of the product mixture, by which is contemplated separation of the beta-limit dextrin from lower molecular weight carbohydrates using a membrane or other suitable separation medium that is effective for this purpose. Generally, a membrane having a molecular weight cut off (MWCO) of 10,000 or less, preferably a MWCO of 5000 or less, is suitable. Suitable commercially available membranes are available from Syndar Filtration and from Osmonics De Sal. Upon ultrafiltration, the retentate typically will include the desired dextrin and some retained low molecular weight sugar (typically maltose). If desired, the retentate may be diafiltered to recover additional maltose by flushing the filter with excess water.

The product thus formed has numerous desirable properties, including a high molecular weight, for instance, a molecular weight of at least 30,000 Daltons and ranging up to 600,000 Daltons, in some cases higher, depending on the starch used as a starting material. The product further has a low DE (and hence a low reactivity and susceptibility to color change), and, surprisingly, a high degree of solubility with very low hazing, even at high molecular weights. Numerous commercial uses are contemplated, including use as a viscosifier. In such applications, the limit dextrin may be added to a product to be made more viscous, in any amount effective for this purpose. It is further contemplated that the dextrin prepared in accordance with the invention can be added to a solution of maltose or of another carbohydrate, or to a dry maltose or other carbohydrate product in an amount sufficient to enhance spray drying of the solution or dry product. In this embodiment, the dextrin preferably is added in an amount ranging from about 5% to about 70% dry solids basis per dry weight of the maltose or other carbohydrate to form a mixture. The mixture may contain other ingredients besides the carbohydrate to be spray dried and limit dextrin, some of which ingredients also may function to enhance spray drying of the maltose.

Carbohydrate percentages given herein are expressed on a dry solids basis per total carbohydrate weight.

The following examples are provided to illustrate the invention, but should not be construed as limiting in scope.

EXAMPLE 1

This example illustrates the preparation of limit dextrin from waxy corn starch.

Starch from waxy corn was made to an aqueous slurry containing 12 to 15% solids and pH 6.0 to 7.0. The slurry was then liquefied by jet cooking through a Hydro Thermal Jet (Model #M103-030) at 300° F., 60 to 65 psi with a 5 minute residence time at 300° F., 50 to 55 psi. The liquefact was immediately cooled, the pH was adjusted to 5.5 with hydrochloric acid, and dosed with beta-amylase. Using a commercial barley beta-amylase enzyme (Genencor OPTI-MALT BBA), dosing was 6.15 DP units per kilogram of starch or 0.05 wt. % grams of liquid enzyme per gram of dry starch. Saccharification was performed at 140° F. for 4 to 24 hours. The solution was then separated by ultrafiltration through a polysulfone 3000 MWCO membrane (Syndar Filtration). The permeate, containing approximately 6% solids, was then evaporated to 70% solids which contained not less than 95% maltose. Beta-limit dextrin was recovered from the retentate.

EXAMPLE 2

This Example illustrates the preparation of beta-limit dextrin from wet mill processed yellow dent corn starch under various liquefaction conditions.

Dent corn starch was liquefied under various reaction conditions, as given in the following Table.

| Example | % solids | pH | Temp (F.) | Residence Time (mm) |
|---------|----------|------|-----------|---------------------|
| 2A | 15 | 3.5 | 300 | 5 |
| 2B | 20 | 3.0 | 300 | 5 |
| 2C | 20 | 2.75 | 300 | 5 |
| 2D | 25 | 2.75 | 300 | 5 |
| 2E | 25 | 3.0 | 300 | 20 |
| 2F | 25 | 2.75 | 300 | 20 |
| 2O | 30 | 3.0 | 300 | 20 |
| 2H | 30 | 2.75 | 300 | 20 |
| 2I | 30 | 3.0 | 300 | 20 |
| 2J | 30 | 3.0 | 280 | 20 |

The pH of the starch was adjusted where necessary, and then was saccharified with a beta-amylase enzyme as in Example 1. The product was centrifuged to remove retrograded amylose. Samples then were filtered through a 3000 MWCO membrane. Beta-limit dextrin was obtained in each case.

EXAMPLE 3

This Example illustrates the liquefaction of wet mill processed yellow dent corn starch with an alpha-amylase enzyme.

In two separate runs, starch from wet mill processed yellow dent corn was adjusted to a solids content of 12 or 25% dry solids basis and the pH was adjusted to pH 5.50 with hydrochloric acid. Each starch slurry was then dosed with a liquefying alpha-amylase enzyme (Novo TER-MAMYL SC) to 0.005–0.02% dry solids basis. The slurries were then jet cooked at 230° to 290° F. with a 5 to 20 minute residence. The alpha-amylase then was quenched by reducing the liquefact pH to less than 4.0 and holding at 180 to 190° F. for 15 minutes. The liquefacts then were saccharified with a beta-amylase enzyme, then filtered and evaporated as in Example 1. Limit dextrin products were obtained.

EXAMPLE 4

This Example describes a scale-up pilot production of beta-limit dextrin.

A commercial yellow dent starch available from Grain Processing Corporation of Muscatine, Iowa (B200) was slurried to a solids level of 15% dsb and a pH of 3.5 with hydrochloric acid. The slurry was fed at a rate of 2 gpm through a Hydroheater jet Series M103 AS at a pressure of 60 psi and a temperature of 300° F. The post-jet residence time was 7.5 minutes resulting in a primary liquefact of a Shell Cup viscosity (Norcross Corp.) of 25 cp. The pH of the liquefact was continuously adjusted to 5.5 with soda ash and cooled through a heat exchanger to 140° F. The liquefact was dosed with Spezyme BBA (Genencor International, Inc.) at a level of 0.05% dsb and converted at temperature through an 8-stage plug flow reactor with continuous agitation and a total residence time of eight hours. The saccharified product was clarified by passing the product through a NIRO Model-C ceramic filtration unit with a 19-element Membrelox, 0.8 um ceramic bundle. The clarified permeate was then ultrafiltered through a NIRO Model-U ultrafiltration unit containing De Sal G-50 membranes. Beta-limit dextrin was recovered from ultrafilter retentate in each case.

EXAMPLE 5

This Example illustrates crystallization of retrograded amylose from the saccharified starch mixture.

The saccharified solution prior to centrifugation from Example 2 was held at 130° F. for 18 to 24 hours. This hold time was necessary for the slow, complete formation of amylose crystals. This saccharified mixture was then pre-filtered through a minimal microfilter of porosity 0.1 to 0.8 micron (U.S. Filter ceramic membranes). The filtration was performed at temperatures not greater than 140° F. to maintain the insoluble retrograded amylose. The filter pore size was selected to produce maximum flux with minimum turbidity in the permeate. For a process using 15% dry solids starch feed at pH 3.5, a 0.8 micron filter will adequately clarify the feed material.

The retentate from the pre-filtration was enriched in the amylose faction and the permeate contained maltose and beta-limit dextrin. Analysis of the amylose particle size using a Malvern Instruments Ltd. Mastersizer showed that 90% of the amylose crystals were of a size between 1 and 20 microns. The crystal size distribution appears to broaden and decrease in size as the process increases in solids and decreases in pH. At a 25% solids content and pH of 3.0, a 0.1 micron filter is necessary for minimal clarification.

The permeate from the microfiltration step was then ultrafiltered as previously described, yielding beta-limit dextrin.

EXAMPLE 6

This Example illustrates that various membranes may be used in the separation of limit dextrin from the product formed upon enzymatic saccharification.

Material was processed through the microfiltration step as described in Examples 4 and 5. Laboratory scale samples were processed on a hollow fiber unit from A/G Technology Corp. (AGT UFP-3-C-4A 3000 NMWC). This filter was run with a Masterflex peristaltic pump (model 7553-70) with a Masterflex head (model 70 15-52) connected with Norprene tubing (model 6402-15). Recirculation rates were adjusted to maintain pressures between 10 psi and 20 psi.

Large scale samples were tested on commercially available spiral wound elements installed and operated on a NIRO Inc. Model R16 Single Stage UF/RO Pilot Plant. Elements evaluated were purchased from Syndar Filtration (PES 3000 MWCO VT2B3838) or Osmonics De Sal (GH/G-10, GK/G-20 and GM/G-50 3838). Operating conditions were those specified by the membrane manufacturer, as follows:

| Membrane | MWCO | Solids |
|---|---|---|
| AGT3000 | 3000 | 25 |
| Syndar 3000 | 3000 | 14 |
| DesalG10 | 2500 | 25 |
| DeSal G20 | 3500 | 25 |
| DeSal G50 | 8000 | 25 |

A beta-limit dextrin product was obtained from the retentate in each case.

EXAMPLE 7

This Example demonstrates the ability to spray dry maltose syrups of various compositions.

Maltose syrup was prepared as described in Example 2 using a 15% dsb starch feed. Three compositions were evaluated, including the ultrafilter feed material that contained 65% maltose and 35% limit dextrin (the "65/35 material"), the ultrafilter permeate material that contained 95% maltose and 5% limit dextrin (the "95/5 material"), and a blend of these materials that contained 90% maltose and 10% limit dextrin (the "90/10 material"). These solutions were spray dried on a Yamoto-Ohkawara Spray Dryer DL-41 with a 2850-SS nozzle and a 65-5 SS orifice. Operating conditions were: drying air 0.75 m³/min, atomizing air 0.25 Mpa, feed rate 20 ml/min, inlet temperature 300° C. outlet temperature 100° C. The feed solids were from 6% to 30% dsb for the 65/35 and 90/10 material. The dry powder produced from these two products contained moisture content of 2–3%. The 95/5 material melted in the receiver line at these temperatures but was effectively dried at reduced temperature of 200° C. inlet temperature, 80° C. outlet temperature with a resulting moisture content of 2.5%.

EXAMPLE 8

This Example illustrates the characterization of beta-limit dextrin and amylose fractions.

Ultrafilter and microfilter retentates from Example 5 were diafiltered on an ultrafilter to remove all permeable material. Samples of both the diafiltered retentates and the crude saccharified liquor were analyzed by aqueous gel permeation chromatography using a modification of the method taught in L. A. Bello-Parez et al., *J. Cereal Sci*, 27 (1998) 267–68, which involves DMSO extraction. A Waters 515 pump connected to a # X PL-Aquagel-OH mixed 8 um column with a separation range of 100 to 10,000,000 Daltons was used. Detection of separated material was done using a Viscotec T^ Dual detector in parallel with a Water 2410127 detection. Data was analyzed with the Viscotec GPC Trisec™ software.

Sample 8A was the crude non-microfiltered saccharified material. Sample 8B was the retentate from a 0.8 um microfiltration with subsequent diafiltration on an ultrafilter. Sample 8C was the permeate from a 0.8 um microfiltration, with subsequent diafiltration on a 3000 MWCO membrane.

The following results were obtained.

| Sample # | Mn | Mw | Mz | Pd |
|---|---|---|---|---|
| 8A | 171000 | 1671000 | 4822000 | 9.77 |
| 8B | 39000 | 51000 | 65100 | 1.3 |
| 8C | 8630 | 28400 | 55800 | 3.29 |

In Sample 8A, it is believed that the high molecular weights result from aggregation of molecules in the concentrate.

EXAMPLE 9

The limit dextrin and retrograded amylose products prepared in accordance with Example 2 were analyzed by gel permeation chromatography as discussed in Example 8, giving the following results.

| Description | Sample | Mn | Mw | Mz | Pd |
|---|---|---|---|---|---|
| Amylose pellet | 2B | 25300 | 226100 | 902000 | 8.94 |
| Amylose pellet | 2C | 12400 | 37400 | 111200 | 3.02 |
| Amylose pellet | 2D | 22000 | 104600 | 324200 | 4.75 |
| Amylose pellet | 2E | 12500 | 62500 | 199600 | 5.00 |
| Amylose pellet | 2F | 3730 | 25600 | 127700 | 6.86 |
| Amylose pellet | 20 | 13500 | 105900 | 425700 | 7.84 |
| Amylose pellet | 2H | 12400 | 27300 | 58800 | 2.20 |
| Limit dextrin | 2B | 63300 | 546700 | 1623000 | 8.64 |
| Limit dextrin | 2C | 19000 | 52300 | 128300 | 2.75 |
| Limit dextrin | 2D | 25200 | 116700 | 330500 | 4.63 |
| Limit dextrin | 2E | 32300 | 130300 | 322700 | 4.03 |
| Limit dextrin | 2F | 11900 | 39800 | 100100 | 3.34 |
| Limit dextrin | 2G | 23800 | 97200 | 253300 | 4.08 |
| Limit dextrin | 2H | 13600 | 36200 | 77900 | 2.66 |

All molecular weight and polydispersity values were calculated by excluding the maltose fraction in the beta-limit dextrin from the integration The following table summarized the effect of liquefaction on the molecular weight of the limit dextrin/amylose fraction from a 3000 MWCO separation. It is noted that the molecular weight of both the limit dextrin and amylose varied in accordance with the liquefaction conditions.

| Sample | Description | Mw | Pd | Maltose |
|---|---|---|---|---|
| 2F | Amylose pellet | 25600 | 6.86 | 84.8 |
| 2H | Amylose pellet | 27300 | 2.2 | 84.9 |
| 2C | Amylose pellet | 37400 | 3.02 | 89.9 |
| 2E | Amylose pellet | 62500 | 5 | 89.4 |
| 2D | Amylose pellet | 104600 | 4.75 | 93.8 |
| 2G | Amylose pellet | 105900 | 7.84 | 91.6 |
| 2B | Amylose pellet | 226100 | 8.94 | 96 |
| 2H | Limit dextrin | 36200 | 2.66 | 84.9 |
| 2F | Limit dextrin | 39800 | 3.34 | 84.8 |
| 2C | Limit dextrin | 52300 | 2.75 | 89.9 |
| 2G | Limit dextrin | 97200 | 4.08 | 91.6 |
| 2D | Limit dextrin | 116700 | 4.63 | 93.8 |
| 2E | Limit dextrin | 130300 | 4.03 | 89.4 |
| 2B | Limit dextrin | 546700 | 8.64 | 96 |

It is thus seen that the invention provides a process for the preparation of dextrins from starch. The process of the invention can be simple and inexpensive to perform, and yields a dextrin with numerous desirable properties. The dextrins can have a high molecular weight. The dextrins are soluble and are stable to haze formation.

While particular embodiments of the invention have been shown, it will be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention. All references and pending applications cited herein are hereby incorporated by reference in their entireties.

What is claimed is:

1. A method for preparing a dextrin product, comprising:

treating a starch with an enzyme that consists essentially of a beta-amylase enzyme under conditions suitable to form a product mixture that includes a dextrin, retrograded amylose, and at least one sugar having a degree of polymerization less than 10;

allowing at least a portion of said retrograded amylose to crystallize from said mixture;

separating the crystallized retrograded amylose from said mixture; and recovering a dextrin rich fraction from said product mixture via ultrafiltration.

2. A method according to claim 1, wherein said dextrin is beta-limit dextrin.

3. A method according to claim 1, further comprising liquefying said starch with an alpha-amylase enzyme and quenching said alpha-amylase enzyme prior to treating said starch with said beta-amylase enzyme.

* * * * *